(12) United States Patent
Bordoloi et al.

(10) Patent No.: US 8,846,849 B2
(45) Date of Patent: Sep. 30, 2014

(54) TISSUE SEALANTS FROM PLASMA DERIVED PROTEINS

(75) Inventors: Binoy K. Bordoloi, Bridgewater, NJ (US); Joseph Zavatsky, Flemington, NJ (US); Chetan Anirudh Khatri, Belle Mead, NJ (US); Olajompo Moloye-Olabisi, Neshanic Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 611 days.

(21) Appl. No.: 13/107,375

(22) Filed: May 13, 2011

(65) Prior Publication Data

US 2012/0288530 A1 Nov. 15, 2012

(51) Int. Cl.
*C08G 63/668* (2006.01)

(52) U.S. Cl.
USPC .............................. 528/300; 523/118; 514/1.1

(58) Field of Classification Search
USPC .............................. 528/300; 523/118; 514/1.1
IPC ................... C08G 63/668,63/40; C09J 167/02, C09J 167/00; A61K 38/16, 38/36, 38/363
See application file for complete search history.

(56) References Cited

U.S. PATENT DOCUMENTS

| 6,371,975 | B2 | 4/2002 | Cruise et al. |
|---|---|---|---|
| 6,833,408 | B2 | 12/2004 | Sehl et al. |
| 7,666,803 | B2 | 2/2010 | Shetty et al. |
| 7,868,123 | B2 | 1/2011 | Khatri et al. |
| 2007/0280988 | A1 | 12/2007 | Ludwig et al. |
| 2008/0220047 | A1 | 9/2008 | Sawhney et al. |
| 2009/0131938 | A1 | 5/2009 | Khatri et al. |
| 2009/0246238 | A1 | 10/2009 | Gorman et al. |
| 2010/0068196 | A1 | 3/2010 | Nur et al. |
| 2010/0173843 | A1 | 7/2010 | Hnojewyl |
| 2011/0086175 | A1 | 4/2011 | Dey et al. |

FOREIGN PATENT DOCUMENTS

WO      WO 99/66964      12/1999

OTHER PUBLICATIONS

International Search Report dated Jul. 10, 2012 re: PCT/US2012/036929.

*Primary Examiner* — David Lukton

(74) *Attorney, Agent, or Firm* — David R. Crichton; Leo B. Kriksunov

(57) ABSTRACT

The present invention is directed in one embodiment to a tissue adhesive or sealant composition comprising an electrophilic group containing cross-linking compound having a linker moiety of a diglycolic acid, a water soluble core moiety and an electrophilic group that is covalently bonded to the diglycolic acid linker moiety and a nucleophilic group containing protein. In other embodiments, the present invention is directed to a delivery device or a medical device on which the composition has been applied or incorporated therein. The present invention is also directed to a method for sealing tissue using the tissue adhesive or sealant composition.

15 Claims, 13 Drawing Sheets

TISSUE SEALANTS FROM PLASMA DERIVED PROTEINS

FIELD OF THE INVENTION

The invention relates to tissue adhesives or sealants formed from a nucleophilic plasma protein, such as fibrinogen, and a cross-linking agent comprising a di-acid linker on which a water soluble core, such as a bifunctional tertiary amine or polyethylene glycol, and an electrophile, such as N-hydroxy succinimide, are attached.

BACKGROUND OF THE INVENTION

Biologic sealants comprising fibrinogen and thrombin are known. Cross-linked fibrin sealant is formed when fibrinogen and thrombin are mixed together but the formed fibrin sealant is subject to undergo enzymatic degradation with plasmin. Such sealants degrade and absorb in about 4 to 7 days, while the sealant mechanical strength and tissue bonding ability must be retained until the wound heals, which can take up to about 14 days. One method for controlling fibrin sealant enzymatic degradation has been by incorporating tranexamic acid or aprotinin into the tissue sealant formulation components. Other means have been explored for improving the strength of fibrin-based adhesive/sealants, such as incorporating collagen.

Published PCT Publication WO1999/066964 by Tammishetti et al. entitled "Carbodiimide cross-linked albumin for bioadhesives, surgical sealants, and implantable devices", teaches a method for producing a cross-linked albumin composition for use in a bioadhesive, surgical sealant or implantable device, comprising the steps of: (a) providing an albumin preparation; (b) providing a carbodiimide preparation; and (c) mixing said albumin preparation and said carbodiimide preparation under conditions which permit cross-linking of said albumin.

U.S. Pat. No. 6,371,975 by Cruise et al. entitled "Compositions, systems, and methods for creating in situ, chemically cross-linked, mechanical barriers" discloses a biocompatible and biodegradable barrier material is applied to a tissue region, e.g., to seal a vascular puncture site. The barrier material comprises a compound, which is chemically cross-linked without use of an enzyme to form a non-liquid mechanical matrix. The compound preferably includes a protein comprising recombinant or natural serum albumin, which is mixed with a polymer that comprises poly(ethylene) glycol (PEG), and, most preferably, a multi-armed PEG polymer.

U.S. Pat. No. 6,833,408 by Sehl, et al. issued Dec. 21, 2004 teaches a method of repairing damaged tissue in a patient comprising the steps of: placing into contact with the damaged tissue an adhesive composition comprised of (i) a hydrophilic polymer; (ii) a crosslinkable component having several nucleophilic groups; and (iii) a crosslinkable component having several electrophilic groups capable of reaction with the nucleophilic groups to form covalent bonds, wherein crosslinkable components are biocompatible and nonimmunogenic, and at least one of components is hydrophilic polymer, and cross-linking of the composition results in a biocompatible, nonimmunogenic, cross-linked matrix.

U.S. Pat. No. 7,868,123 by Khatri and Bordoloi, issued Jan. 11, 2011 and entitled "Derivatized tertiary amines and uses thereof" teaches tertiary amine intermediate and electrophilic monomers derived therefrom. The invention also relates to adhesives or sealants derived from such electrophilic moieties.

Published U.S. Patent Application No. 2008/0220047 by Sawhney et al. published Sep. 11, 2008 and entitled "Low-swelling biocompatible hydrogels" teaches surgical treatment for treating a tissue inside a vertebral column by forming a low-swelling biodegradable hydrogel in situ that is adherent to a tissue inside the vertebral column. Sawhney et al. teaches a method comprising: forming a low-swelling biodegradable hydrogel by in situ polymerization that is adherent to tissue inside a vertebral column and substantially exterior to a theca in the vertebral column, wherein the first functional groups comprise nucleophiles and the second functional groups comprise electrophiles, wherein the first synthetic precursor is selected from the group consisting of dilysines, trilysines, and tetralysines, wherein the second synthetic precursor comprises a multi-armed precursor possessing a core and arms, the arms each comprising a polyethylene glycol having a molecular weight from about 250 to about 5000, wherein the core is selected from the group consisting of polyethers, polyamino acids, proteins, and polyols, and wherein forming the hydrogel comprises reacting a first synthetic precursor comprising at least three of a first functional group with a second synthetic polymer precursor comprising at least three arms that each comprise a second functional group, wherein the first functional group reacts with the second functional group to form covalent crosslinks between the first synthetic precursor and the second synthetic polymer precursor, and wherein the hydrogel swells upon exposure to a physiological solution.

Published U.S. Patent Application No. 2007/0280988 by Ludwig et al. published Dec. 6, 2007 and entitled "Coating layers for medical devices and methods of making the same" teaches methods for controlling the morphology and the release-rate of active agent from coating layers for medical devices comprising a polymer matrix and one or more active agents. The methods comprise fixing the morphology or phase distribution of the active agent prior to removing solvent from the coating composition. The coating layers can be used for controlled delivery of an active agent or a combination of active agents.

Published U.S. Patent Application No. 2010/0173843 by Hnojewyj entitled "Tissue Adhering Compositions" discloses a method which mixes a first component, a second component, and a buffer material. The first component includes an electrophilic polymer material comprising poly (ethylene glycol) having a functionality of at least three. The second component includes a nucleophilic material comprising a natural or synthetic protein at a concentration of about 25% or less that, when mixed with the first component within a reaction pH range, cross-links with the first component to form a non-liquid, three-dimensional barrier. The buffer material includes tris-hydroxymethylaminomethane having a pH within the reaction pH range. The method applies the mixture to adhere to a tissue region.

SUMMARY OF THE INVENTION

Figure 1:
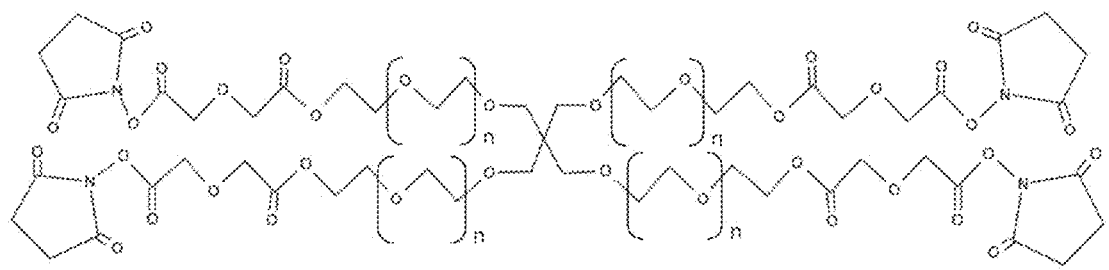
FIG. 1 shows 4-Arm PEG-tetra Diglycolate-tetra-NHS ester or PEG-Diglycolate-NHS Active Ester (also designated simply PEG-DG-N).

The present invention is directed in one embodiment to a tissue adhesive or sealant composition comprising an electrophilic group containing cross-linking compound of formula 1

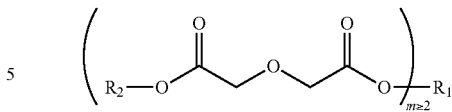

[1]

having a linker moiety of a diglycolic acid, a water soluble core moiety $R_1$ and an electrophilic group $R_2$ that is covalently bonded to the diglycolic acid linker moiety and a nucleophilic group containing protein. The water soluble core moiety $R_1$ is derived from compounds selected from the group consisting of bifunctional tertiary amines and polyethylene glycols and has at least two "m" side chain arms that are covalently bonded to said diglycolic acid linker moiety. The nucleophilic group containing protein is preferably derived from blood plasma, such as fibrinogen. The fibrinogen can be in the form of a lyophilized particle. Examples of preferred bifunctional tertiary amines are TKHEED or TKHPED, which are described more fully in U.S. Pat. No. 7,868,123 which is incorporated herein by reference in its entirety for all purposes, while the polyethylene glycol is preferably a polyethylene glycol having at least four side chain arms.

In one embodiment, the electrophilic moieties $R_2$ are NHS end groups such that the electrophilic group containing cross-linking compound of formula 1 above is represented by the compound of formula 2 or formula 3

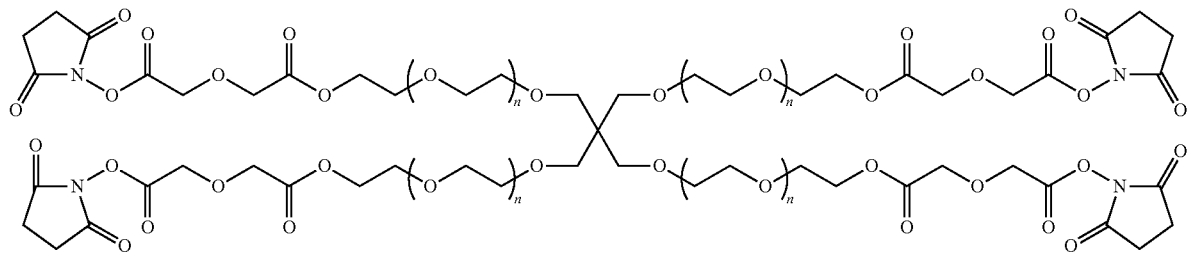

[2]

where "n" is a number within the range 5-100; more preferably within the range of 15-25, more preferably on average n is about 20;

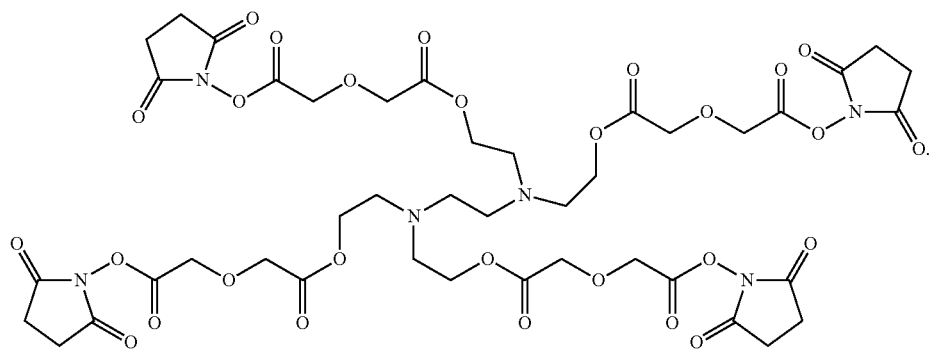

[3]

The tissue adhesive or sealant can be in a dry powder form prior to contact with the moisture or with a tissue to which the adhesive or sealant is applied. The tissue adhesive or sealant can be disposed on an absorbable or non-absorbable substrate for purposes of delivery in a treatment setting, such as a surgical procedure. The tissue adhesive or sealant can be in the form of a solution of the electrophilic group containing cross-linking compound and a solution of the nucleophilic group containing protein which are maintained separately prior to use in a medical application and are admixed for use in the medical application. Alternatively, the tissue adhesive or sealant can be a dry powdered form of the electrophilic group containing cross-linking compound and the nucleophilic group containing protein.

In another embodiment, the present invention is directed to a delivery device having at least a first and a second chamber; wherein the electrophilic group containing cross-linking compound is contained in said first chamber and the nucleophilic group containing protein is contained in the said second chamber, and wherein the electrophilic group containing cross-linking compound and the nucleophilic group containing protein are expressed from said first chamber and said second chamber and are mixed thus forming said tissue adhesive or sealant. The moisture that enables the reaction between the electrophilic group containing cross-linking compound and the nucleophilic group containing protein can be supplied at least in part by the moisture in the application setting, particularly from the surrounding tissue.

In another embodiment, the present invention is directed to a medical device, such as a suture, staple, vascular graft, suture knot clip, orthopedic pin, clamp, screw, plate or clip on or in which the tissue adhesive or sealant described above has been coated, sprayed, incorporated or other applied.

The present invention is also directed to a method for sealing tissue by using a cross-linking agent having a linker moiety comprising a diglycolic acid, a water soluble core moiety selected from the group consisting of bifunctional tertiary amines or polyethylene glycols and having a plurality of side chain arms with at least two of the side chain arms covalently bonded to the linker moiety and an electrophilic moiety that is covalently bonded to the linker moiety and a nucleophilic group containing protein component and reacting said crosslinking agent with the nucleophilic group containing protein in the presence of moisture to form an adhesive or sealant, and contacting the adhesive or sealant with a tissue surface prior to, during, or after reacting the crosslinking agent with the nucleophilic group containing protein in the presence of moisture.

DETAILED DESCRIPTION OF THE INVENTION

The present invention is directed to an adhesive and/or sealant composition comprising a nucleophilic plasma-derived protein and a crosslinking agent having an electrophilic group that reacts with the nucleophilic groups on the plasma-derived protein to form a proteinaceous network, such as a fibrinogen matrix. A fibrinogen matrix is composed primarily of interconnected and agglomerated fibrinogen as opposed to fibrin matrixes that are derived primarily from strands of fibrin derived from the activation of fibrinogen by thrombin in the conventional clot cascade sequence. The adhesive or sealant composition according to the present invention has multiple medical applications and may be used in many types of surgery, including, but not limited to, gastrointestinal, cardiovascular, peripheral-vascular, cardio-thoracic, gynecological, neuro- and general abdominal surgery.

For example, the adhesive or sealant composition may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. These compositions can also be used as an adhesive for lung volume reduction, patch fixation, subcutaneous tissue repair, and aortic dissection. In one embodiment, these compositions can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the adhesive or sealant compositions described herein can be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the adhesive or sealant compositions described herein can be used as a sealant to attach and seal dural patch products, bile duct, bile leaks in liver bed, bladder leaks, bone graft, burn graft dressing and liquid occlusive dressing. As a sealant, the compositions can be coated on tissue, device, and tissue-device interface and be used as dural—cranial sealant, dural—spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant, hemostats combination, urethra sealant. These compositions can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder bed sealing, and cholecystectomy. Additionally, the adhesive or sealant compositions may be coated on medical devices such as sutures or staples.

Fourth, the adhesive or sealant compositions can be used as a filler or a periurethral bulking agent in procedures including, but not limited, to dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophogeal fistula.

Fifth, the adhesive or sealant compositions can be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and nutraceuticals, localization matrix for chemotherapy, and localization matrix for contrast agent.

Sixth, the adhesive or sealant compositions can be used as an adhesion prevention barrier in procedures such as cardiac, open chest, general surgery, obstetrics and gynecological surgeries, orthopedic surgeries, and spine (e.g. artificial disk).

Seventh, the adhesive or sealant compositions can be used as an occluding material for embolization (e.g. GI Fistula, cerebral/vascular occlusive brain aneurism, tubal occlusion, and varicose vein occlusion).

According to an embodiment of the present invention, a substantially free of added thrombin-free cross-linked fibrinogen based sealant is prepared using a novel system of electrophilic crosslinking agent in an aqueous environment. The sealant forms hydrogels having desirable attributes for tissue sealants. A dry powder blend of the cross-linker and the biologically active component (BAC-2), comprising mostly fibrinogen, but also containing other plasma derived proteins including albumin, quickly forms a sealant upon hydration when applied over wet tissue. Mechanical performance data for the sealant show excellent bonding over wet Corium tissue. When applied over an incision in a gastro-intestinal (GI) segment, the sealant demonstrates desirable resistance to fluid leak under pressure. The instant sealant, unlike thrombin initiated fibrin clot, does not undergo enzymatic degradation by plasmin, but rather forms a network hydrogel system that is hydrolytically degraded and is absorbed due to the incorporation of ester links via the multi-arm cross-linker.

For purposes of the present applications, the phrase "substantially free of added thrombin" means the sealant or adhesive composition contains insufficient amounts of thrombin to initiate conversion of fibrinogen to fibrin in an aqueous environment. However, it should be noted that thrombin will naturally be present in the environment in which the tissue sealant or adhesive is applied.

All proteins derived from plasma by fractionation are nucleophilic in nature due to the presence of lysine and arginine residues in the protein. Important fractionation products of relevance here are albumin and fibrinogen. They may be used in the form of either solution or lyophilized powder.

The crosslinking agent used in the present compositions is a derivative of acid group containing compound, preferably a derivative of a diacidic compound, having a water-soluble group and an electrophilic group. According to an embodiment of the present invention, an NHS (N-hydroxy succinimide) derivative of an acid compound known as an active ester compound is used that reacts rapidly with water or nucleophilic moieties. The cross-linker system of the instant invention is the preferably a diglycolic acid active ester wherein an NHS end group has reacted via its N-Hydroxyl functionality with the di-acid or by using any other suitable reagent, for example a carbonate. The reaction binds NHS end group with the carboxylic functionality of the di-acid. The di-acid may in turn be further bonded to the water soluble core entity via the reaction of the other carboxyl group of the di-acid and the hydroxyl functionality of the water soluble core entity. In preferred practice, the water soluble core entity is first reacted with an anhydride of the di-acid. This derivatized acid is then converted to active ester by capping the free carboxyl group with the NHS end group. The resulting diglycolate active ester cross-linker derivatives have been found to provide (i) a rapid cure with a nucleophilic containing plasma-derived proteins, such as a fibrinogen-containing solution, and (ii) a relatively extended adsorption period as a sealant and/or adhesive.

PEG (polyethylene glycol) and non-PEG based water-soluble cores having varying side-chain arms and different di-acid starting compounds have been used for synthesizing cross-linking agents suitable for use in the present invention. A preferred cross-linking agent is TKHEED-Diglycolate-NHS (or T-DG-N, tetrakis-hydroxyethylethylene diamine-diglycolate-NHS).

The inventors discovered that the sealant resulting from the reaction of fibrinogen-containing plasma derived protein composition and the preferred active ester described above has (a) ease of use with one step for preparation, (b) gelation or cure rate of 1 to 2 minutes (and 3 minutes for Peel test), (c) normal handling for making of patches containing sealant coating and testing of said patches, (d) stability in enzymatic environment and longevity of a few weeks in hydrolytic medium at pH 7.4 and 37° C., and (e) desirable mechanical properties of 90° Peel adhesion and Hydraulic Burst Leak Test (HBLT) to bovine Corium and in-vivo acute burst on porcine GI segment.

According to an embodiment of the present invention, a tissue sealant is provided having the properties of rapid curing in 1-2 minutes or less forming a sealant upon hydration of dry powder and having an absorption profile suitable for GI wound healing (about 2 weeks).

In one embodiment, the present enzymatically non-degradable sealant is made from fibrinogen without significant conversion to fibrin by being substantially free of any addition of thrombin to the site of application. In one embodiment, the hydrolytically degradable cross-linked fibrinogen-based sealant cross-links via the diglycolate active ester cross-linker.

In one embodiment, the present sealant system can be used on absorbable or non-absorbable matrix, backing, supporting scaffold, or pad wherein a sealant powder blend is deposited over the matrix forming a patch, with demonstrated excellent ex vivo mechanical performance of tissue peel and burst strengths. In one embodiment, the dry sealant blend with its electrophile component having a glass transition temperature (Tg) of about 20° C. resulting in good retention of the blend on the matrix and reduced sloughing off of the sealant powder from the supporting matrix.

According to an embodiment of the present invention, the sealant composition demonstrates rapid hydration of two-component formulations and ability to rapidly react with protein providing significant peel and burst strength.

According to an embodiment of the present invention, the sealant composition can be combined with collagen or gelatin for improved sealant strength.

According to an embodiment of the present invention, the fibrinogen-based sealant composition is employed in combination and/or dispersed on a woven or non-woven substrate having an oxidized polysaccharide, such as oxidized cellulose, more preferably oxidized regenerated cellulose.

According to an embodiment of the present invention, a tissue adhesive or sealant composition forms upon contact with moisture or tissue by reaction of a nucleophilic protein, preferably plasma-based, more preferably plasma-derived, most preferably a fibrinogen and a cross-linking agent comprising di-acid acid ester crosslinker to which a water soluble core and an electrophile are bonded. A cross-linked fibrinogen-based sealant can be made from a fibrinogen-containing composition and a synthetically made cross-linker without the use of added thrombin. The resulting novel sealant would not be expected to undergo enzymatic degradation with plasmin due to the absence or reduction in the amount of fibrin in the resulting matrix. The fibrinogen matrix portion would be expected to be absorbed via ester hydrolysis at the ester links formed by diglycolic acid ester cross-linking reaction.

According to an embodiment of the present invention, the tissue sealant cross-linking system is an NHS (N-Hydroxy Succinimide)-containing electrophile that forms an "activated ester" link with a carboxylic acid, and which reacts rapidly with nucleophiles, producing a new covalent link by eliminating the condensation by-product of NHS. This chemistry is compatible in an aqueous medium. The electrophile reacts with the nucleophilic moiety of primary amines in plasma derived biologic proteins producing amide links; for example, the lysine residues in fibrinogen and albumin will react with the electrophile. Human fibrinogen with a molecular weight of 340,000 g/mole has 208 lysine residues, and human albumin with a molecular weight of 67,000 g/mole has about 60 lysine residues. A crosslinking agent with at least two electrophilic moieties is needed to form an interconnecting network of nucleophilic proteins and to make a sealant of the instant invention. Increasing the number of side-chain arms of the electrophilic moieties in the crosslinking agent increases the probability of the curing reaction, and thus the speed of cure and the degree of cross-linking. According to an embodiment of the present invention, cross-linking agents with two, four, or more side-chain arms are used, with such a cross-linked biologic sealant being degradable and absorbable after the wound healing period.

According to an embodiment of the present invention, ester units are built into the crosslinking agent such that the cross-linked nucleophilic protein can undergo hydrolysis at the ester links producing linear protein molecules with carboxylic acid groups bound via amide links that are water soluble.

According to an embodiment of the present invention, the crosslinking agent is a compound having two or more side-chain arms of active ester links of NHS and a core moiety structure with a high degree of water solubility.

According to an embodiment of the present invention, the crosslinking agent comprises:
(1) a water soluble core moiety of
  (I) PEG (polyethylene glycol) with two or more side-chain arms; or
  (II) bi-functional tertiary amine with four side-chain arms with hydroxyl functionality, such as (a) N,N,N',N'-tetrakis(2-hydroxyethyl)ethylenediamine (TKHEED), or (b) N,N,N',N'-tetrakis(2-hydroxypropyl)ethylenediamine (TKHPED, Quadrol);
(2) a di-carboxylic acid moiety for covalently linking with each arm of the water soluble core moiety producing one ester link and one carboxyl end group, such as,
  (I) diglycolic acid,
  and
(3) an NHS moiety as an end group linking with each carboxyl moiety of the arm, to form an activated ester electrophile.

The resultant adhesive or sealant forms when it is exposed to or in contact with moisture or tissue in presence of a nucleophilic protein, such as fibrinogen. It may be desirable to use the adhesive or sealant components in powder or solid form, with or without a substrate. Further, the adhesive or sealant components can be used in a powder or solid form in combination with a knitted, woven or nonwoven matrix or substrate of oxidized regenerated cellulose (ORC), glycolide-lactide copolymers or a combination thereof. Suitable substrates for use with the adhesive or sealant components can be absorbable or nonabsorbable.

The resultant polymer composition can also function as a coating that is applied to any medical device, including but not limited to, sutures, staples, vascular grafts, suture knot clip, orthopedic pins, clamps, screws, and plates, clips (e.g., for vena cava). For example, the medical device can be coated with a solution of the nucleophilic moiety followed by a coating with a solution of the electrophilic moiety, and the nucleophilic and electrophilic moieties are allowed to react to form a cross-linked polymer that functions as a coating on the device. In the case of a suture or staple, it may be desirable to have a coating that swells upon contact with physiological fluid after the suture or staple is used to close a wound, thereby sealing the hole that is formed from a suture needle or the staple. Therefore, it may be preferable to utilize PEG-containing component, since PEG-based materials swell upon contact with moisture, particularly water.

Five exemplary crosslinking agents have been shown to form suitable tissue sealant of the instant invention. Two of the exemplary crosslinking agents, 4-Arm-Quadrol-Diglycolate-NHS (Q-DG-N) and 4-Arm-TKHEED-Glutarate-NHS (T-Glu-N) are described more fully in U.S. Pat. No. 7,868,123, which is incorporated herein by reference in its entirety. Synthesis of three other exemplary crosslinking agents is described below. All five exemplary crosslinking agents were evaluated with a biologic plasma, blood-derived product, known as BAC2 (biologically active component), which contains primarily fibrinogen at about 40% by weight, the rest including albumin, buffers and other protein components conventionally found in blood plasma derived products.

EXAMPLE 1

Synthesis of 4-Arm-PEG-Diglycolate-NHS and its NMR Characterization

Figure 2:
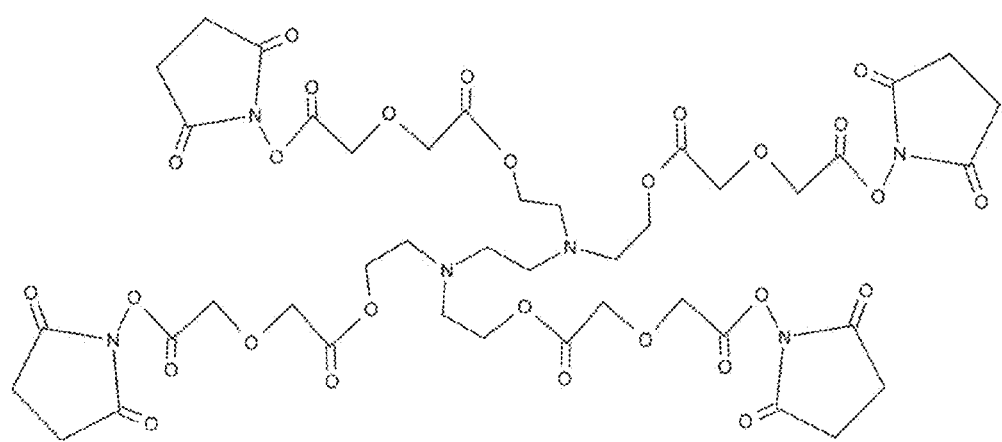
FIG. 2 shows 4-Arm-TKHEED-Digycolate-NHS Active Ester (T-DG-N).

Referring now to FIG. 2, 4-Arm PEG (MW of 4000)-tetra Diglycolate-tetra-NHS ester or PEG-Diglycolate-NHS Active Ester (also simply designated PEG-DG-N), MW=4,800 approximately, is shown.

A 4-arm PEG-4000, made from a pentaerythritol core with its four hydroxyl functionalities combined with ethylene oxide to make the four PEG chains with a total molecular weight of 4000 g/mole, is described here for further derivatization to the cross-linker. 4-arm PEG-4000 (200 g, 0.050 mol) is dissolved in toluene (200 mL) with heating and the solvent is removed in order to azeotropically remove any entrained water in the PEG starting material. The residue is re-dissolved in anhydrous toluene (500 mL) at 70° C. and diglycolic anhydride (23.2 g, 0.20 mol). The solution is heated to 95° C. and stirred under a nitrogen atmosphere for 41 hours, cooled, and the solvent is removed in vacuo. The residue is dissolved in water (700 mL) and washed with ether (2×200 mL) then extracted with dichloromethane (5×200 mL). The combined organics are dried over $MgSO_4$, filtered, and the solvent is removed to yield an oily wax. This residue is dissolved in dichloromethane and the solvent is removed to azeotropically remove any residual water, then re-dissolved in anhydrous dichloromethane (750 mL). N-Hydroxysuccinimide (23.2 g, 0.21 mol) was added with stirring and then N,N-dicyclohexylcarbodiimide, known as DCC, (42.3 g, 0.21 mmol) is dissolved in dichloromethane (200 mL) and dripped in over 1 hour. The reaction mixture gradually became cloudy and warmed to reflux. The mixture is stirred to room temperature overnight. A milky white heterogeneous mixture is filtered, and the residue concentrated to approximately 500 mL total volume and ether added (1000 mL). An oily residue is separated and the top organic layer decanted. The remaining oily material is dissolved in anhydrous acetone (200 mL) and ether (1 L) is slowly added with stirring. The material is tightly capped and stored overnight at −10° C. The bottom layer becomes a milky white waxy solid that is isolated and placed on high vacuum at room temperature (3 days) (205 g yield, 85%). The material is a white waxy solid that can be broken into chunks at room temperature. It is stored under a nitrogen atmosphere at −10° C. The material was characterized by $^1$H-NMR ($CDCl_3$). Residual acetone, DCC and ether were not detected by NMR analysis. Residual NHS was calculated to be 1.4% (w/w) by $^1$H-NMR integration.

EXAMPLE 2

Synthesis of TKHEED-Diglycolate-NHS and its NMR Characterization

Figure 3:
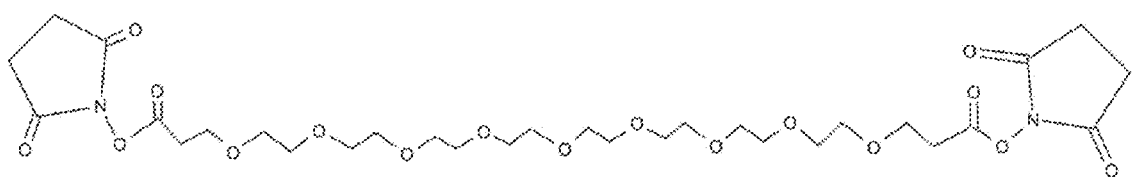
FIG. 3 shows 2-Arm-PEG-Diacid-NHS Active Ester (PEG-NHS).

Referring to FIG. 3, 4-Arm TKHEED-tetra Diglycolate-tetra-NHS ester or TKHEED-Diglycolate-NHS (or simply T-DG-N), where TKHEED is N,N,N',N'-tetrakis(2-hydroxyethyl)ethylenediamine, is shown. TKHEED, (25 g, 106 mmol) and ethoxyquin (1 g) is dissolved in dry acetonitrile (150 ml) and pyridine (75 ml) under a nitrogen atmosphere. Diglycolic anhydride (50 g, 431 mmol) is added. There is an exotherm and the mixture becomes homogeneous. The solution is then stirred at ambient temperature for 3 hours. Disuccinimidyl carbonate (120 g, 468 mmol) is then added and the reaction stirred at ambient temperature overnight. The reaction evolves gas and the disuccinimidyl carbonate's slowly dissolved to provide a clear solution. The solvents are removed under reduced pressure and the residue is dissolved in dry acetonitrile (100 ml). Two portions (40 ml) of the solution are placed in two 250 ml sized centrifuge bottles and of isopropyl alcohol (175 ml) is added to each bottle. The mixture is stirred and then centrifuged. The liquid top layer is decanted and the residue from each bottle was taken up in dry acetonitrile (25 ml). The procedure is repeated three more times. After four treatments with isopropyl alcohol, the residue in each bottle is dissolved in dry acetonitrile (25 ml) and a 60:40 ethyl acetate/heptane mixture (175 ml) added. The mixture is stirred and then centrifuged. The top layer of liquid is decanted and the procedure is repeated. The residue in each bottle is directly transferred to a 2 l flask. The product is dried to an off-white foam under high vacuum for 3 days. The remainder of the material is processed in an identical manner to give a total of 85 g (75%) of product. The foam is crushed and transferred to a plastic bottle, and stored under a nitrogen atmosphere at −10° C. The Tetra-NHS ester was prepared from TKHEED, diglycolic anhydride, and NHS carbonate in acetonitrile to yield the product along with residual NHS and a small amount of acetonitrile and ethyl acetate. The overall purity as characterized by NMR integration was: T-DG-N 84.4%, Free NHS 13.9%, Acetonitrile 1.3%, and Ethyl acetate 0.39%.

EXAMPLE 3

PEG-Diacid-NHS

Figure 4:
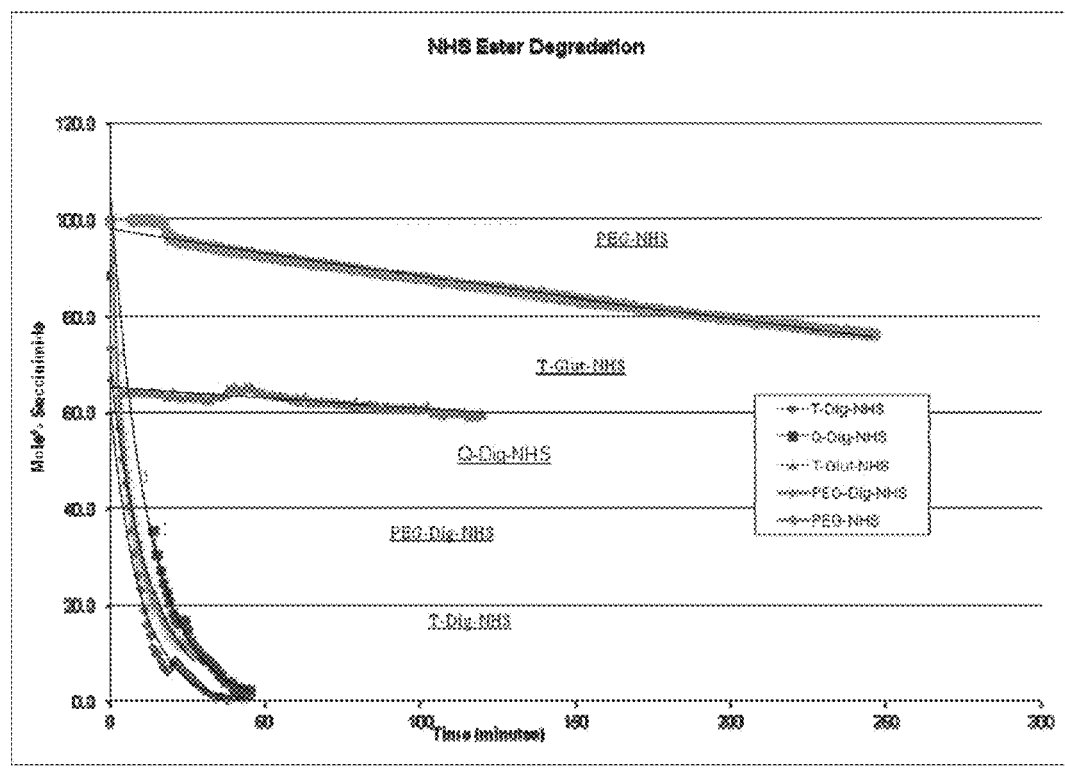
FIG. 4 shows hydrolysis rates in $D_2O$ at 25° C.

Referring to FIG. 4, 2-Arm-PEG-NHS Active Ester or PEG-Diacid-NHS, also known as Bis-dPEG(9)-NHS ester, MW=708 g/mole (Quanta Biodesign Ltd., Ohio). The compound can be synthesized, for example, from the corresponding PEG diol, whereby the two primary alcohol end groups of a PEG diol are oxidized to form two carboxylic acid end groups, which are then derivatized to form the NHS end groups.

EXAMPLE 4

Methodologies for Formulation of Crosslinking Agent with BAC-2 and Patch Preparation Exemplary crosslinking agents, which are described above, were evaluated with BAC-2 in a powdered blend. Mechanical performance was characterized in the form of a patch. Various methods utilized in sample processing are described below.

Cryo-Milling

A freezer mill for liquid nitrogen assisted cryo-milling was used on T-DG-N and PEG-DG-N crosslinking agents. Process parameters included T1/Grinding time of 3 minutes, T2/Cooling time of 2 minutes, T3/Pre-cooling time of 15 minutes, and Cyc/No. of Cooling cycles 6. Powdered BAC-2, a blood plasma derived product was obtained from Omrix BioPharmaceuticals and can be produced as described in US Published Patent Application 2011/0086175, US Published Patent Application 2010/0068196 and US Published Patent Application 2009/0246238, all of the foregoing publications are hereby incorporated by reference in their entirety. Particulate collagen was made from INSTAT MCH hemostat commercially available from Ethicon, Inc.

Dipping Station with HFE-7000 Solvent for Patch Making

A vacuum assisted automated dipping station, known as manual controlled immersion method machine (mCiM) that is suitable for making 2×4 square inch patches was used. Each 2×4 square inch unit was comprised of a layer of Interceed™ ORC that was needle-punched with Vicryl™ staple yarns. HFE-7000 solvent was used to prepare a powder slurry/suspension preparation containing the crosslinking agent and nucleophilic protein. 7 to 8 ml of the suspension was applied onto each matrix unit. The dipping process and equipment is described more fully in the US Published Patent Application 2011/0086175 which is incorporated herein by reference in its entirety for all purposes.

Further details on patch preparation are also described under Example 8.

Particle Size Distribution Characterization

An LS 13 320 Beckman Coulter particle size analyzer was used for particle size characterization of T-DG-N crosslinking agent, the BAC-2 component, and particulate collagen.

Mechanical Performance Evaluation of Patches

Several methods described below were utilized for characterizing the mechanical performance of the resulting matrix units.

The 90° Peel Adhesion Test:

The standard test as per AST-20089-0121 was the most commonly used method. The standard moisture activation time of 3 minutes for cure was used for all patch samples and a control unit.

HBLT (Hydraulic Burst Leak Tester):

A cutter for stamping out of test specimen of a fixed diameter was used. Harvested Corium tissue was kept in a saline medium. A defect of 4 mm was made at the center of Corium with a biopsy punch. A medium of saline with a syringe pump at a constant flow rate, a 500 μL volume of saline for test specimen wetting before patch application, and two 500 μL aliquots after patch application to Corium were used. Upon sealant curing with a dwell time of 5 minutes after patch application to Corium, testing was initiated.

Acute In Vivo Test:

For the acute in vivo test, the patch or powder was applied over a 10 mm incision with a single suture knot on a segment of a porcine gastrointestine tube. Air pressure was applied for inflation and the leak pressure was noted.

Enzymatic Degradation Studies

Sealants based on the inventive compositions were prepared by using an aqueous solution of BAC-2 (about 7% fibrinogen, or 70 mg/ml) where the crosslinking agent in the form of a powder was added at a selected composition and mixed well for 1 to 2 minutes up to gellation.

Hydrolytic Degradation Studies

Sealant with ester links undergoing hydrolytic degradation in PBS at 37° C. was evaluated by the % weight loss method. Sealant degradation in de-ionized (DI) water causes the pH level of the solution to rise, which can be titrated by addition of a basic compound to maintain a constant pH of 7.4 at 37° C. until such time that no more basic compound was needed to maintain a neutral solution; the total time for titration was noted.

80 to 100 minutes. The presence of residual acid due to prior hydrolysis shows the initial drop for the glutarate.

The data further demonstrates that diglycolic linker unexpectedly results in faster hydrolysis of corresponding esters degrading more than 95% in 30 to 60 minutes irrespective of core structure. As will be shown below, corresponding degradation of cross-linked protein with a diglycolate cross-linker will be relatively rapid and suitable for absorption as a tissue sealant. It is anticipated that such a cross-linked sealant will display in vitro degradation rate faster than that from a glutarate cross-linker, but will likely be slower than that from an enzymatic degradation mechanism.

Hydrolysis degradation parameters are summarized in Table 1 qualitatively from the chart in FIG. 4. It is observed that the Relative Rate, m, (in the exponential equation) for all the Diglycolate-NHS esters are within about 20% of each other. However, the rates are much faster than the others; for example, T-Dig-NHS (or T-DG-N) is 144 times faster than T-Glut-NHS, and 98 times faster than PEG-NHS. The degradation profiles of cross-linker A (T-DG-NHS), B (Q-Dig-NHS) and C (PEG-Dig-NHS) correspond to the instant invention, while the crosslinking agent D (T-Glut-NHS) and E (PEG-NHS) correspond to control groups.

TABLE 1

Summary of Qualitative and Quantitative Parameters of Hydrolysis in $D_2O$ at 25° C.

| NHS ester cross-linker | Estimated Time for 10% Hydrolysis (minute) | Estimated Time for 95% Hydrolysis (minute) | % Hydrolysis, $y = k\,Exp(-mx)$ where, $x$ = Time, $m$ = Relative Rate, $k$ = Constant, $R^2$ = Correlation co-efficient |
|---|---|---|---|
| (A) 4-Arm-TKHEED-Diglycolate-NHS (T-Dig-NHS) | — | 30 | $k = 62$; $m = 0.104$; ($R^2$ = 96%) |
| (B) 4-Arm-Quadrol-Diglycolate-NHS (Q-Dig-NHS) | — | 60 | $k = 107$; $m = 0.084$; ($R^2$ = 99%) |
| (C) 4-Arm-PEG-Diglycolate-NHS (PEG-Dig-NHS) | — | 60 | $k = 70$; $m = 0.079$; ($R^2$ = 97%) |
| (D) 4-Arm-TKHEED-Glutarate-NHS (T-Glut-NHS) | 100 | — | $k = 65$; $m = 0.00072$; ($R^2$ = 81%) |
| (E) 2-Arm-PEG-Diacid-NHS (PEG-NHS) | 80 | — | $k = 98$; $m = 0.00106$; ($R^2$ = 99%) |

EXAMPLE 5

Determination of Relative Rates of Reactivity of Active Esters by NMR

The relative reactivity of the active esters was determined by monitoring the rate of hydrolytic degradation in $D_2O$ at room temperature by NMR as shown in FIG. 4.

Various NHS active esters shown in FIG. 4 are the 4-Arm-TKHEED-Diglycolate-NHS (T-Dig-NHS or T-DG-N), the 4-Arm-Quadrol-Diglycolate-NHS (Q-Dig-NHS or Q-DG-N), the 4-Arm-PEG-Diglycolate-NHS (PEG-Dig-NHS or PEG-DG-N), the 4-Arm-TKHEED-Glutarate-NHS (T-Glut-NHS or T-Glut-N), and the 2-Arm-PEG-Diacid-NHS (PEG-NHS). It was observed that diglycolate-containing esters are the fastest hydrolyzing active esters, meaning to hydrolyze more than 95% in about 30 to 60 minutes irrespective of the core structure. The glutarate or the PEG-diacid based agents, which do not have the alpha-ether link of diglycolate or diglycolic acid, hydrolyze at much slower rates. These compounds appear to hydrolyze only about 10% or less in about

EXAMPLE 6

Qualitative Rates of Gelation of BAC-2 Solution with Active Ester Crosslinking Agent Data on cure speed or qualitative rates of gelation of various active esters in forming sealants with an aqueous solution of fibrinogen (BAC-2) are shown in Table 2 below. Crosslinking agents A, B, C correspond to the instant invention, while D and E correspond to control groups. The solid NHS ester, preferably in a powder form, was added to the BAC-2 solution at room temperature in a test tube at a weight ratio of 1 to 1 for active ester to fibrinogen, and mixed well. The time for gelation, defined qualitatively as the point when the BAC-2 solution in the test tube no longer flowed, was noted and recorded as shown in Table 2. It is observed that the various Diglycolate-NHS active esters gelled in about 1 to 2 minutes, PEG-Diacid-NHS ester in about 15 to 30 minutes, and Glutarate-NHS ester in about 30 to 60 minutes. Thus the diglycolates were the fastest gelling crosslinking agent irrespective of their core structure. The cores of TKHEED, Quadrol or PEG with their varying molecular weights or equivalent weights or the presence or absence of tertiary amines did not seem to make any difference.

The TKHEED was considered a better core than Quadrol as the former diglycolate-NHS ester had very high water solubility, more than 85%, as compared to only about 25% for the latter. The four hydrophobic methyl groups in Quadrol lowered the aqueous solubility significantly.

The TKHEED based diglycolate-NHS was found to be a better cross-linker for its ease of handling as powder as compared to the PEG based diglycolate-NHS, which was a waxy and sticky material. TKHEED with its two tertiary amine moieties was expected to have a catalytic effect on the electrophile—nucleophile cure reaction unlike the PEG crosslinker.

TABLE 2

Qualitative Rates of Gelation of a Fibrinogen Solution with Active Ester Cross-linkers

| NHS ester cross-linker | Cross-linker equivalent weight, approx. | Weight ratio of Cross-linker to Fibrinogen content in solution (at 70 mg/ml, approx.) | Qualitative observation of Gelation (minute) |
|---|---|---|---|
| 4-Arm-TKHEED-Diglycolate-NHS (A) | 250 | 1:1 | 1-2 |
| 4-Arm-Quadrol-Diglycolate-NHS (B) | 260 | 1:1 | 1-2 |
| 4-Arm-PEG-Diglycolate-NHS (C) | 1,200 | 1:1 | 1-2 |
| 4-Arm-TKHEED-Glutarate-NHS (D) | 250 | 1:1 | 30-60 |
| 2-Arm-PEG-Diacid-NHS (E) | 350 | 1:1 | 15-30 |

EXAMPLE 7

Preparation of the Patch

The dipping station for patch preparation is described under Example 5 (B). Material handling aspects are described in further details here. Sealant compositions of diglycolate crosslinking agent were optimized against their mechanical properties of bonding to tissue and degradation rates in aqueous environment of physiological relevance.

A matrix comprising Interceed™ oxidized regenerated cellulose (ORC) knitted fabric and Vicryl™ staple yarns needle-punched into it was utilized. Contents of Interceed™ and Vicryl™ were 50% and 50% by weight in the matrix. Each matrix unit had two directions designated as 'Longitudinal' (L) and 'Transverse' (T), depending on the direction of the knitted structure. Each matrix unit, also referred to as reinforced absorbable multilayered fabric, is described more fully in the U.S. Pat. No. 7,666,803 by Shetty et al., teaching a multilayered fabric comprising a first absorbable nonwoven fabric and a second absorbable woven or knitted fabric, which is incorporated herein by reference in its entirety.

For the test patch described as "TDGN Patch" or "T-DG-N Patch", 4-Arm-TKHEED-Diglycolate-NHS (T-DG-N or TDGN) was cryo-milled to a fine powder. The particle size was 569+/−263 micron (<90% 827 and <10% 136 micron), though the largest sizes appeared to be agglomerates. The powder was stored in the refrigerator below its glass transition temperature of 20° C. and was blended with a fibrinogen-containing composition in powder form in various ratios. The particle size of the powder fibrinogen-containing composition was 20+/−11 micron (<90% 36 micron and <10% 7 and).

A known amount of powder blend was deposited onto the matrix using the mCiM dipping station. The resulting material was stored in a tray case and stored in a sealed foil pouch in a nitrogen box. A silicone release paper was used to prevent sticking of the blend to the plastic case inner surface.

An inventive patch made from 4-Arm-PEG-Diglycolate-NHS is described hereinafter as "PEG-DG-N Patch". Unlike T-DG-N, the PEG-DG-N did not disperse well in HFE-7000 solvent. It had a tendency to phase separate from the fibrinogen powder component in the solvent medium. Therefore, the cryo-milled blend was warmed at 37° C., which was above the melting point of PEG-DG-N, and the resulting paste was applied over the same matrix. Upon transferring to the matrix tray and applying a mild pressure, it became a smooth coating. A silicone release paper was used to prevent sticking to the plastic case.

Peel Adhesion data are discussed below and show comparative results for the PEG-DG-N Patch, and the T-DG-N Patch.

EXAMPLE 8

PEG-DG-N Patch: 90° Peel on Corium

Figure 5:
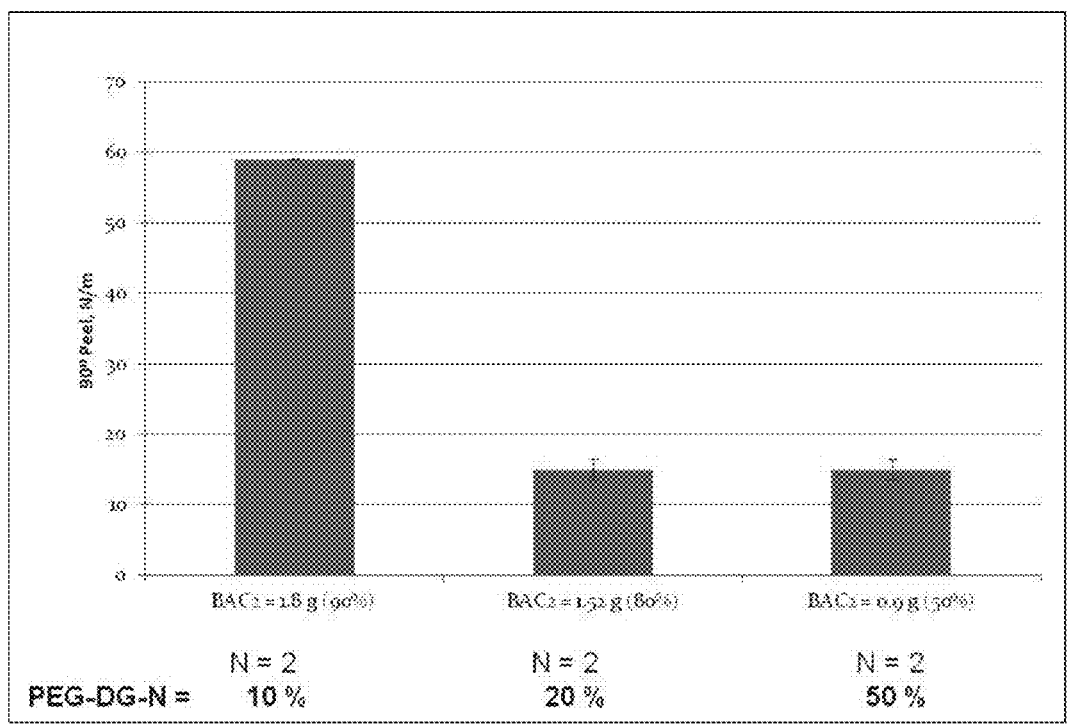
FIG. 5 shows 90° Peel force on Corium (Longitudinal).

The Peel adhesion was tested and the data for the PEG-DG-N Patch is shown in FIG. 5, representing 90° Peel force on Corium (Longitudinal) at 37° C. of PEG-DG-N/Fibrinogen Patches at Coat Weight of 1.8 to 2.0 gm per matrix unit and demonstrating the effect of PEG-DG-N content in weight % on peel force.

Data on the various compositions are shown in Table 3. Compositions containing only a low level of cross-linker, approximately 10 weight %, showed a reasonable bonding to Corium of 59+/−0.1 N/m. Higher cross-linker content appeared to give a lower peel strength, which may be attributed to the larger structure of the cross-linker with a molecular weight 4,800 g/mole (or equivalent weight of 1,200, as shown in Table 2), perhaps creating steric hindrance with fibrinogen.

TABLE 3

PEG-DG-N/BAC-2 Patch: 90° Degree Peel on Corium at 37° C.

| ID # | T or L | PEG-DG-N/BAC2 (Weight % Ratio) | Coat Wt, (gm/unit) | BAC-2 (gm/unit) | N (#) | Peel; Avg. (N/m) | Peel; +/− Std. Dev. (N/m) |
|---|---|---|---|---|---|---|---|
| 2 | L | 10/90 | 2.0 | 1.80 | 2 | 59.0 | 0.1 |
| 3 | L | 20/80 | 1.9 | 1.52 | 2 | 15.0 | 1.5 |
| 4 | L | 50/50 | 1.8 | 0.90 | 2 | 15.0 | 1.5 |
| 5 | T (MC*) | 50/50 | 1.7 | 0.85 | 2 | 17.0 | 1.6 |

*made from Methylene Chloride (dissolves PEG-DG-N) instead of HFE-7000

EXAMPLE 9

T-DG-N Patch: 90° Peel on Corium

The performance data for the T-DG-N/BAC-2 patch are summarized in Table 4. The various parameters of interest include matrix direction, T-DG-N weight % in composition, coat weight per matrix unit, total BAC-2 content per matrix unit, number of replicates in testing, and the average and standard deviation.

TABLE 4

TDGN/BAC-2 Patch: 90° Peel on Corium at 37° C.

Figure 6:
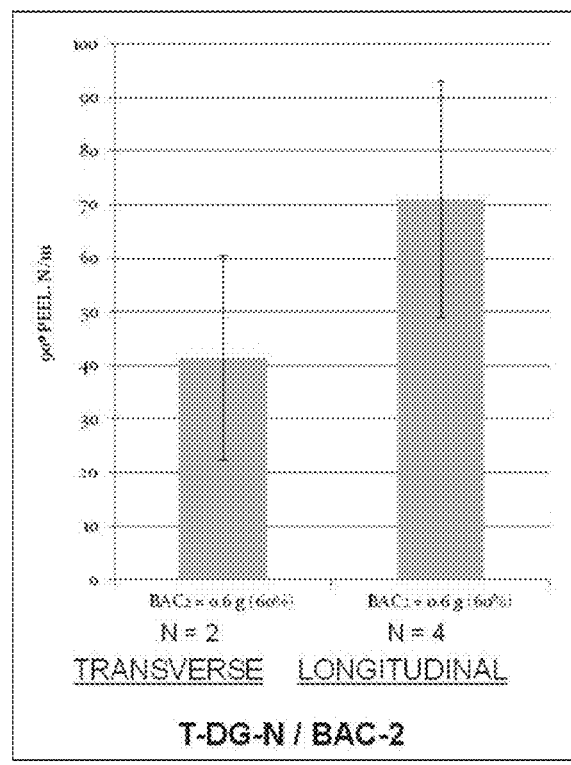
FIG. 6 shows the force for 90° Peel on Corium at 37° C. in Transverse vs. Longitudinal of T-DG-N/BAC-2 Patches.

| ID# | T or L | TDGN/BAC2 (Wt % Ratio) | Coat Weight, (gm/unit) | BAC-2 (gm/unit) | N (#) | Peel; Avg. (N/m) | Peel; +/− Std. Dev. (N/m) |
|---|---|---|---|---|---|---|---|
| 2 | L | 0/100 | 1.0 | — | — | — | — |
| 3 | L | 10/90 | 1.4 | 1.26 | 2 | 50.5 | 7.8 |
| 4 | L | 20/80 | 0.8 | 0.64 | 2 | 44.0 | 11.3 |
| 5A | T | 30/70 | 1.6 | 1.12 | 5 | 106.7 | 27.7 |
| 5B | L | 30/70 | 1.0 | 0.70 | 2 | 44.0 | 9.9 |
| 5C | L | 30/70 | 1.4 | 0.98 | 4 | 84.0 | 7.7 |
| 6A | T | 40/60 | 1.0 | 0.60 | 2 | 41.5 | 19.1 |
| 6B | L | 40/60 | 1.0 | 0.60 | 4 | 71.0 | 22.1 |
| 7A | T | 50/50 | 1.5 | 0.75 | 4 | 90.2 | 13.1 |
| 7B | T | 50/50 | 1.8 (@ 37° C./2 Hrs) | 0.90 | 2 | 73.0 | 5.2 |
| 7C | T | 50/50 | 1.7 (in 2 mos aging, open/close) | 0.85 | 2 | 31.0 | 5.7 |
| 7D | L | 50/50 | 1.3 | 0.65 | 2 | 143.0 | 22.6 |
| 8 | L | 60/40 | 0.7 | 0.28 | 2 | 57.0 | 5.6 |
| 9 | L | 100/0 | 0.9 | 0.00 | 1 | 4.0 | — |
| 10 | L | 33/50/17** | 1.0 | 0.50 | 2 | 46.0 | 0.1 |
| 11 | L | 50/33/17** | 1.5 | 0.50 | 2 | 94.5 | 9.2 | matrix as described above was utilized with TDGN/BAC-2
**= 17% is Particulate Collagen from INSTAT MCH Referring now to Table 4, the effect of 'Longitudinal' vs. 'Transverse' Matrix can be seen. The examples of the T-DG-N Patch (#6) are shown in FIG. 6 representing the force for 90° Peel on Corium at 37° C. in Transverse vs. Longitudinal of T-DG-N/fibrinogen patches. It is observed that the "L" direction consistently gives a higher peel strength than the "T" direction, 69% for 6A vs. 6B, where the coat weight is held constant for a given patch.

Figure 7:
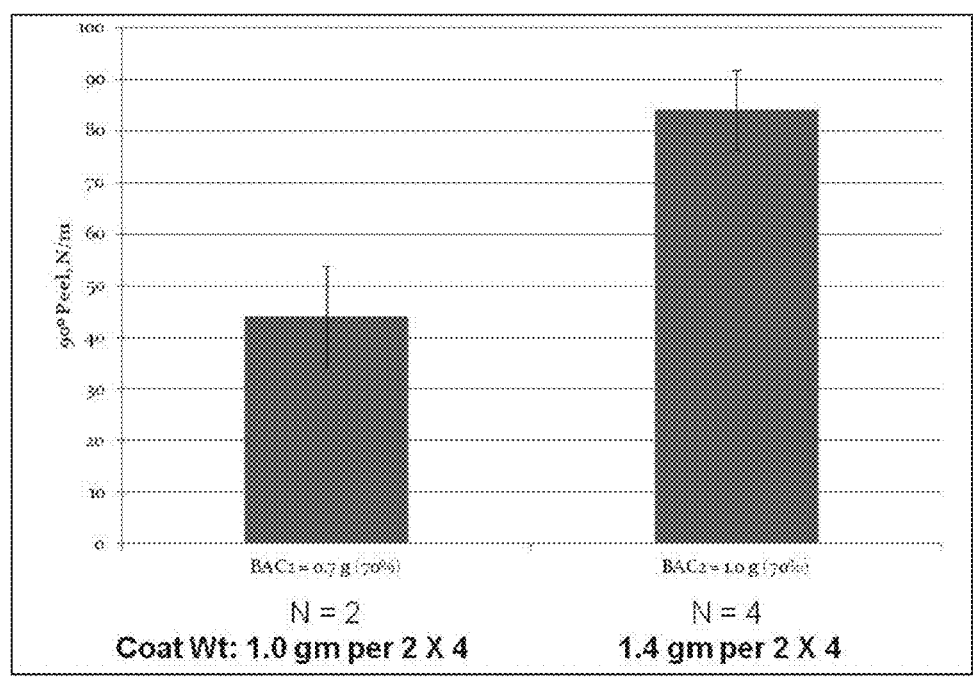
FIG. 7 shows the force for 90° Peel on Corium (Longitudinal) at 37° C.

Referring now to FIG. 7, which shows the force for 90° Peel on Corium (Longitudinal) at 37° C. demonstrating the effect of Coat Weight on T-DG-N/fibrinogen patch, is can be observed that the higher the coat weight for a given composition tested in the same direction, the higher the peel strength; for example Patch 5B vs. 5C of Table 4.

Figure 8:
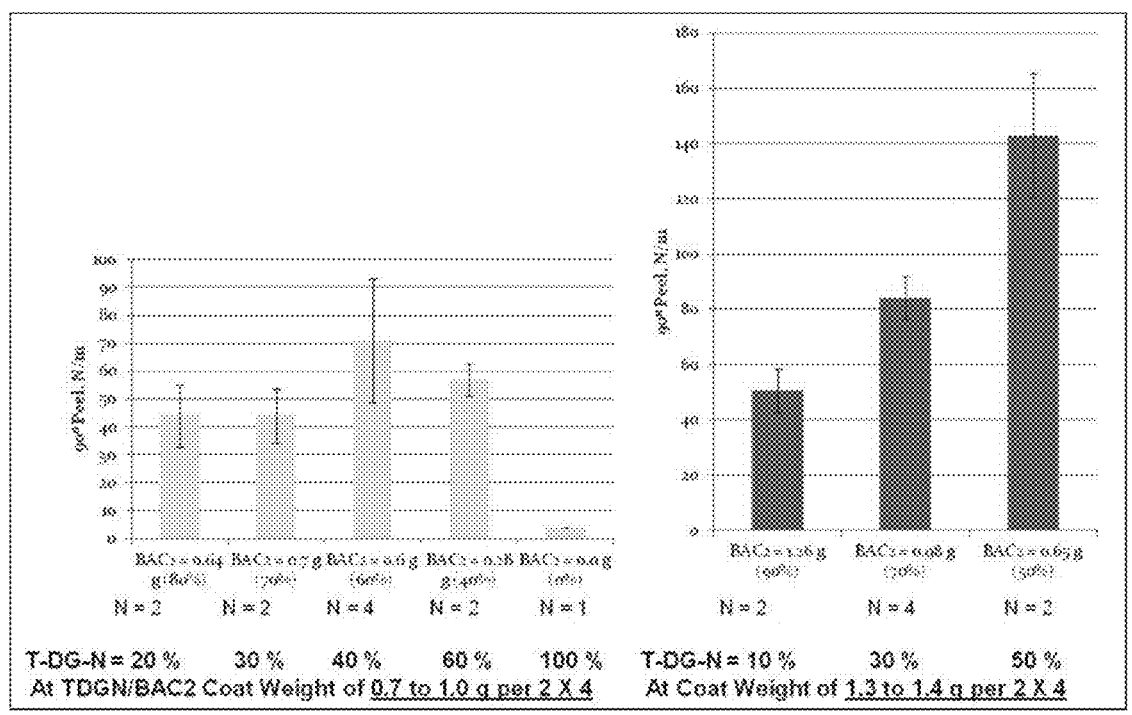
FIG. 8 shows the force for 90° Peel on Corium (Longitudinal) at 37° C.

Referring now to FIG. 8, which shows the force for 90° Peel on Corium (Longitudinal) at 37° C. and demonstrating the effect of Weight % T-DG-N at a Constant Coat Weight (with left chart showing low coat weights and right chart showing high coat weights), the effect of composition at two levels of coat weights can be observed, showing good performance at as low a concentration as 10 weight % T-DG-N. The compositions tested at a reasonably constant coat weight of 0.7 to 1.0 gram per matrix unit over the wide range of compositions show a central tendency of higher performance around 50 weight % T-DG-N. It is clearly observed at the constant coat weight of 1.3 to 1.4 gram per matrix unit that the higher the cross-linker (up to 50 weight %), the higher the peel performance.

Figure 9:
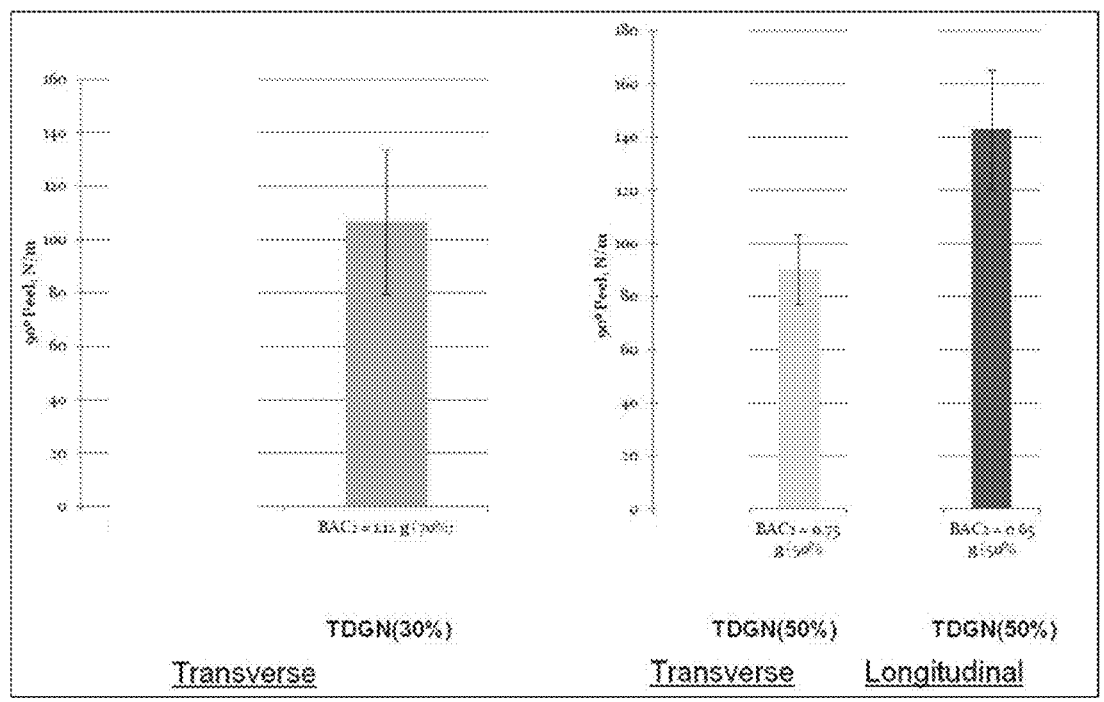
FIG. 9 shows the force for 90° Peel on Corium at 37° C.

Referring now to FIG. 9, which shows the force for 90° Peel on Corium at 37° C. (Transverse or Longitudinal): (A) At 30% TDGN (left chart), (B) At 50% TDGN (right chart). As shown, the TDGN Patch may be formulated with either a lower (e.g. 30%) or a higher (e.g. 50%) level of cross-linker. A lower level of cross-linker obviously has a higher content of fibrinogen as shown. At the higher level of 50 weight % T-DG-N, a statistically significant higher level of performance is observed at a lower content of fibrinogen (0.65 or 0.75 gm). This performance is noted in either the 'L' or the 'T' direction. The cross-linker level may be lowered if the buffer content of arginine and glycine, which is a total of 22 weight % in the fibrinogen composition, can be reduced.

Figure 10:
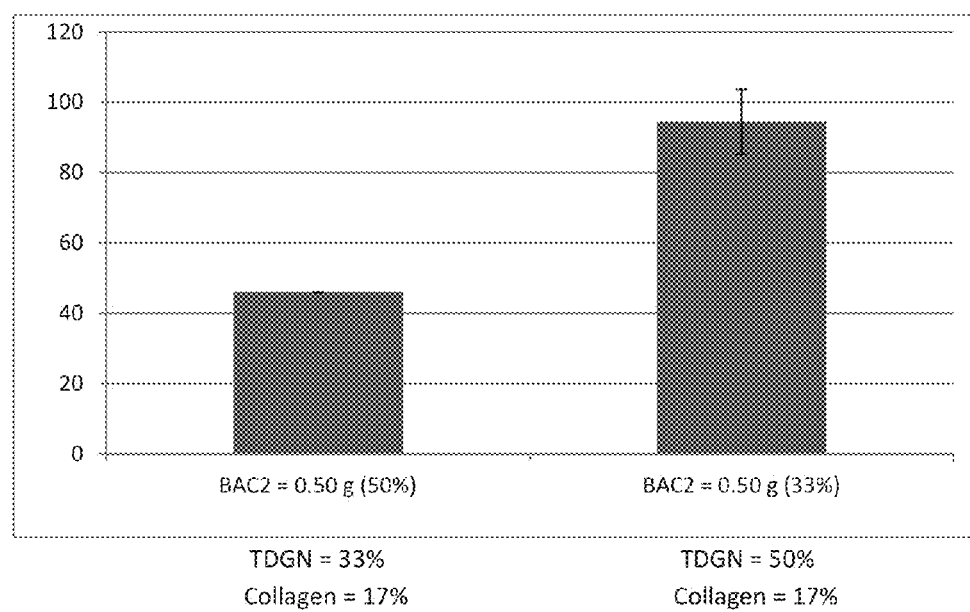
FIG. 10 shows the force for 90° Peel on Corium at 37° C. (Longitudinal).

Referring now to FIG. 10, which shows the force for 90° Peel on Corium at 37° C. (Longitudinal) and demonstrates the effect of TDGN weight % at a Constant Particulate Collagen (INSTAT MCH) level of 17 weight %; fibrinogen content per matrix unit is held constant by adjusting the coat weight. It is demonstrated that the reinforcing effect of collagen made by cryo-milling from INSTAT MCH™ (bovine, available from Ethicon, Inc.), with the particle size being an average of 125+/−79 micron (<90% 238 micron and <10% 28 and). Here the fibrinogen content is held constant by adjusting the coat weight, and keeping a constant level of collagen at 17% by weight. The higher level of 50 weight % TDGN shows a reasonably high level of performance of 95+/−9 N/m peel strength at only 0.5 gram fibrinogen per matrix unit.

EXAMPLE 10

HBLT Performance of Patches

Figure 11:
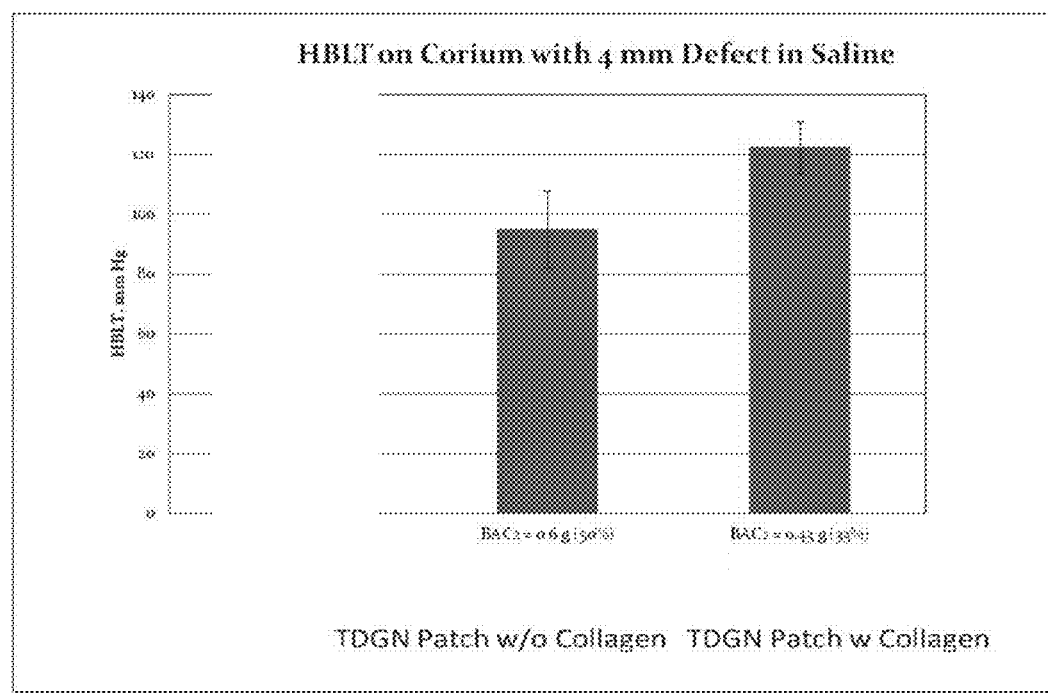
FIG. 11 shows the results of HBLT Burst Test on Corium with 4 mm defect in saline.

HBLT (Hydraulic Burst Leak Test, as guided by ASTM Method F 2392-04, "Standard Test Method for Burst Strength of Surgical Sealants") is another quantitative method to characterize sealant strength. Referring now to FIG. 11, it summarizes data on Corium tissue using the TDGN patches mentioned above. FIG. 14 shows the results of HBLT Burst Test on Corium with 4 mm defect in saline and compared performance of TDGN Patch with and without 17% collagen (INSTAT MCH) at a constant TDGN of 50%. The Corium substrate here has a 4 mm biopsy punch hole for the defect for fluid leak. The TDGN Patch with 50 weight % TDGN shows a leak at 95+/−13 mm Hg (where N=4, a coat weight of 1.2 gram and a fibrinogen content of 0.60 gram per matrix unit).

Here again particulate collagen at a loading of 17 weight % with TDGN of 50 weight % shows the reinforcing effect with a performance of 122+/−9 mm Hg (where N=2 and a coat weight of 1.3 gram) with a fibrinogen content of only 0.43 gram per matrix unit.

EXAMPLE 11

Acute In Vivo Characterization

The TDGN/BAC-2 of 50/50 weight % blend was evaluated here as a powder. An Interceed™ was used as a carrier of the powder blend over the incision on the GI segment. The carrier was left behind and saline was applied over it so that the powder is wetted on the tissue. The carrier bonded well to the porcine GI in about 2 to 3 minutes. This test is done with a 10 mm incision and a single suture knot at the center that showed a burst pressure of about 58 mm Hg, demonstrating increased resistance to fluid leak. A base line leak would be at or below 5 mm Hg.

EXAMPLE 12

Enzymatic Degradation of Sealant by Plasmin at 37° C.

Figure 12:
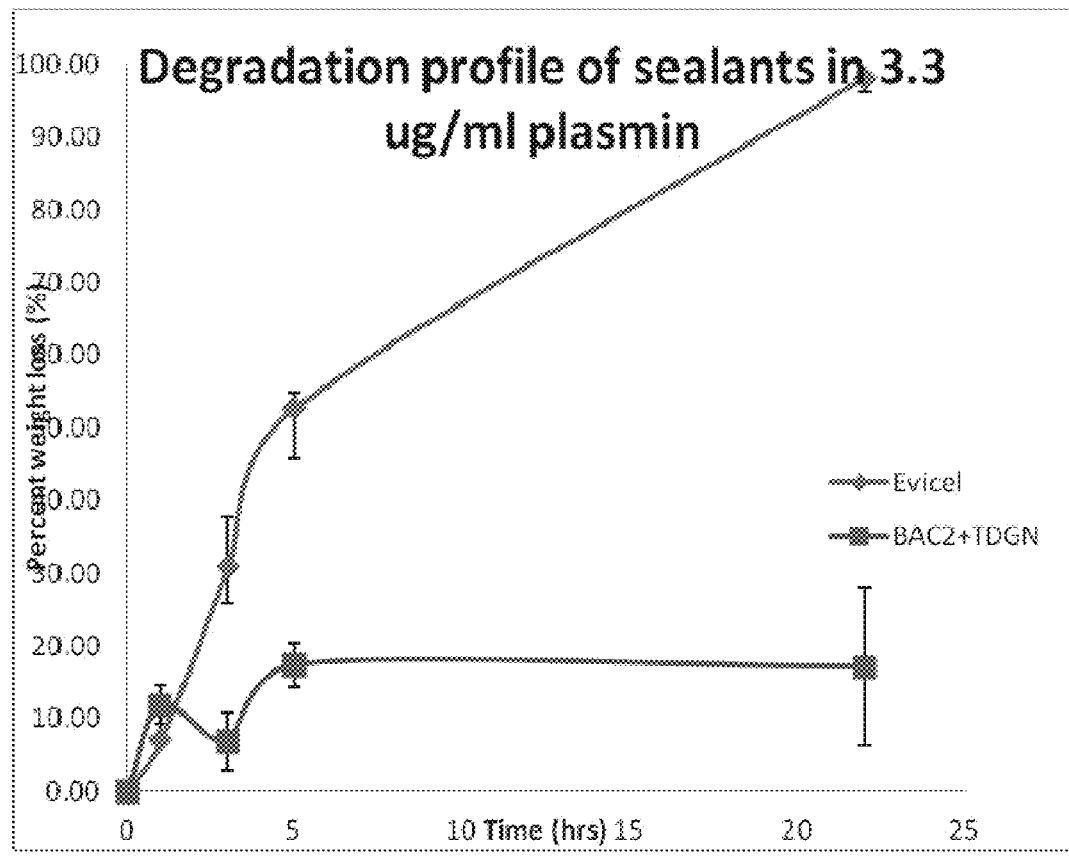
FIG. 12 shows degradation profiles in plasmin solution at 37° C.

Sealants were prepared using an aqueous solution of fibrinogen (about 7% solution), where powder of either T-DG-N or PEG-DG-N was added at a selected composition based on the fibrinogen content. Upon dissolution of the active ester in the fibrinogen solution, a hydrogel formed in about 1 to 2 minutes at ambient temperature. The in vitro rate of degradation of the hydrogel (or sealant) was determined in an enzymatic medium of plasmin at a concentration of 3.3 microgram/ml by determining the % clot remaining by gravimetric method after a given duration of exposure. The data are shown in FIG. 12 in comparison with a fibrin-based clot. FIG. 15 shows a comparison of fibrin-based clot vs. Fibrinogen/TDGN in 3.3 μg/ml plasmin solution at 37° C. It is clearly observed that the NHS ester "cross-linked fibrinogen" shows resistance to enzymatic degradation unlike the thrombin initiated "cross-linked fibrin", where the former degraded 100% in about 22 hours, while in the latter only 20% degraded during the same period.

EXAMPLE 13

Hydrolytic Degradation of Sealant in PBS at 37° C.

Figure 13:
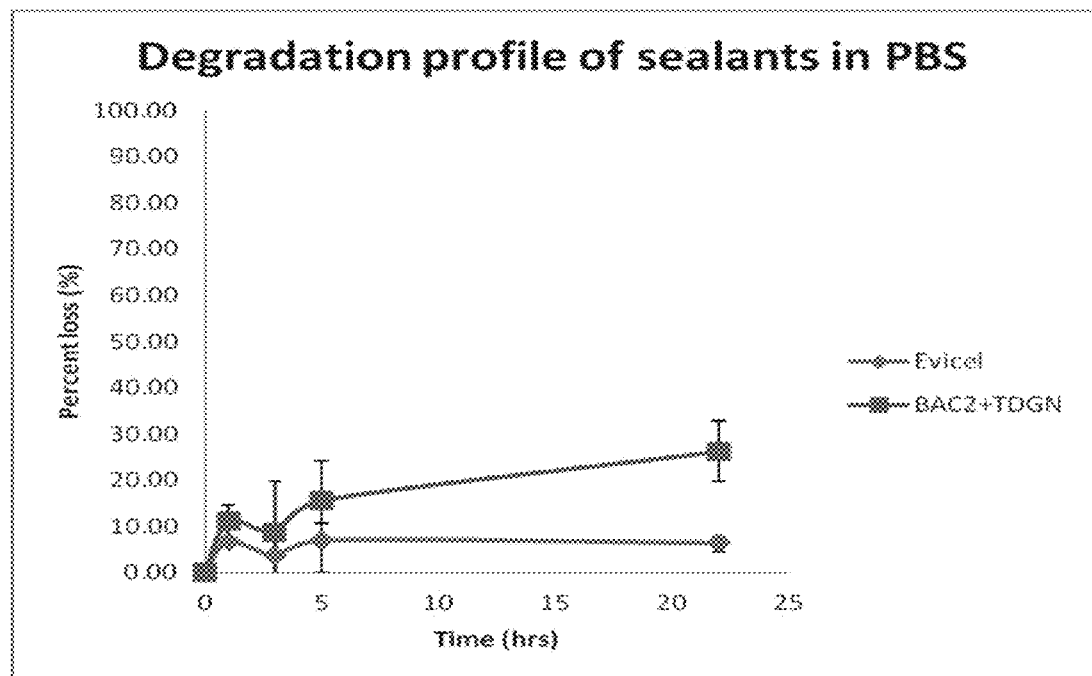
FIG. 13 shows degradation profiles in PBS solution at 37° C.

The degradation of the above two sealants (or clots) were also investigated in a PBS buffer medium, as shown in FIG. 13, which shows a comparison of fibrin-based sealant versus Fibrinogen/TDGN in PBS at 37° C. It was observed that the TDGN began to show some hydrolytic degradation in about 22 hours at 37° C. unlike the fibrin-based sealant.

EXAMPLE 14

Hydrolytic Degradation of Sealant in De-Ionized Water at 37° C.

As the Diglycolate-NHS/BAC-2 system is a hydrogel of fibrinogen with ester based cross-links, its degradation was followed in the pH profiler of de-ionized water at 37° C., where a base was added to neutralize the acid formed upon ester hydrolysis with time, to maintain a constant neutral pH. The data are summarized in Table 5. Cross-linker weight % was varied based on fibrinogen content. Varying in vitro duration of longevity is observed in Table 5 for sealants made from fibrinogen with T-DG-N or PEG-DG-N.

TABLE 5

Longevity of Sealants of Varying Compositions in a Hydrolytic Medium of Deionized Water at 37° C. as Measured by pH Profiling for Maintaining a Constant pH at 7.4

| Type of Diglycolic-NHS Cross-linker | NHS Cross-linker by (wt %) | N (#) | Avg.(Days) | +/− Std Dev (Days) |
|---|---|---|---|---|
| T-DG-N | 30 | 2 | 2.7 | +/−0.4 |
| T-DG-N | 50 | 3 | 7.1 | +/−3.7 |
| T-DG-N | 60 | 1 | 16.7 | — |
| PEG-DG-N | 50 | 3 | 19.8 | +/−8.7 |

We claim:

1. A tissue adhesive or sealant composition comprising:
   (a) an electrophilic group-containing cross-linking compound of formula 1

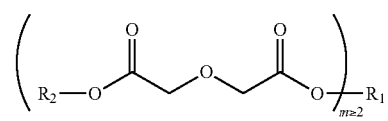

[1]

having
   (1) a linker moiety of a diglycolic acid;
   (2) a water soluble core moiety $R_1$ that is derived from the compounds in the group consisting of tertiary amines and polyethylene glycols, wherein said water soluble core moiety has at least two "m" side chain arms that are covalently bonded to said diglycolic acid linker moiety;
(3) a group $R_2$ that is covalently bonded to a carboxyl group of the diglycolic acid linker moiety forming an active ester electrophile, and
(b) a nucleophilic group-containing protein.

2. The tissue adhesive or sealant composition according to claim 1 wherein the nucleophilic group-containing protein is derived from blood plasma.

3. The tissue adhesive or sealant composition according to claim 1 wherein the nucleophilic group-containing protein is fibrinogen.

4. The tissue adhesive or sealant composition according to claim 3 wherein the fibrinogen is in the form of a lyophilized particle.

5. The tissue adhesive or sealant composition of claim 1 wherein $R_1$ is derived from tertiary amines selected from the group consisting of N,N,N',N'-tetrakis(2-hydroxyethyl)ethylenediamine (TKHEED) or N,N,N',N'-tetrakis(2-hydroxypropyl)ethylenediamine (TKHPED).

6. The tissue adhesive or sealant composition of claim 1 wherein $R_1$ is derived from a polyethylene glycol having at least four "m" side chain arms.

7. The tissue adhesive or sealant composition of claim 1, wherein the $R_2$ electrophilic moieties are NHS end groups such that the electrophilic group-containing cross-linking compound of formula 1 is a compound represented by formula 2 or formula 3

8. The tissue adhesive or sealant composition of claim 2 wherein the tissue adhesive or sealant composition is in a dry powder form prior to contact with a moisture or with a tissue.

9. The tissue adhesive or sealant composition of claim 4 wherein the tissue adhesive or sealant composition is disposed on an absorbable or non-absorbable substrate.

10. A device comprising a first composition and a second composition, wherein said first composition comprises a solution of an electrophilic group-containing cross-linking compound of formula 1,

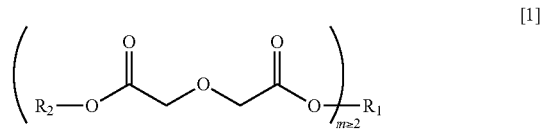

[1]

having
(1) a linker moiety of a diglycolic acid;
(2) a water soluble core moiety $R_1$ that is derived from the compounds in the group consisting of tertiary amines and polyethylene glycols, wherein said water soluble core moiety has at least two "m" side chain arms that are covalently bonded to said diglycolic acid linker moiety;
(3) a group $R_2$ that is covalently bonded to a carboxyl group of the diglycolic acid linker moiety forming an active

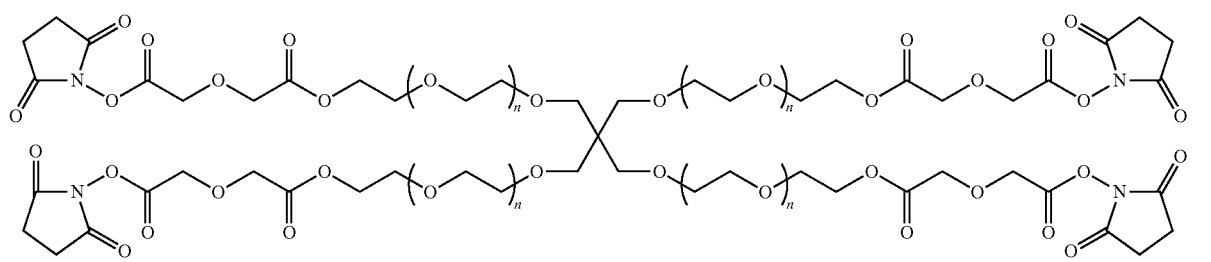

[2]

where "n" is a number within the range 5-100;

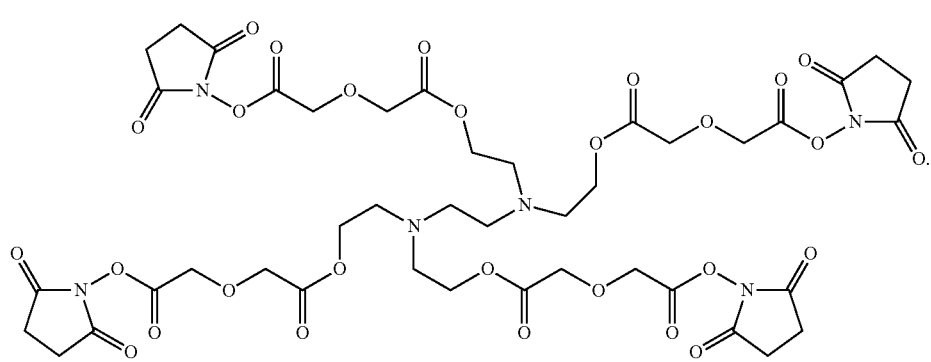

[3]

ester electrophile, and said second composition comprises a fibrinogen, wherein the fibrinogen is in the form of a lyophilized particle wherein said first composition and said second composition are maintained separately prior to use in a medical application and are admixed for use in the medical application.

11. A tissue adhesive or sealant composition comprising a dry powdered form of the electrophilic group-containing cross-linking compound of formula 1 according to claim 1 and a dry powdered form of a nucleophilic group-containing protein.

12. A device of claim 10, further comprising at least a first and a second chamber; wherein the electrophilic group-containing cross-linking compound of formula 1 is contained in said first chamber and the nucleophilic group-containing protein is contained in the said second chamber, and wherein the electrophilic group-containing cross-linking compound of formula 1 and the nucleophilic group-containing protein are expressed from said first chamber and said second chamber and are mixed thus forming a tissue adhesive or a sealant composition.

13. The tissue adhesive or sealant composition of claim 8, wherein the moisture is supplied by the tissue.

14. A medical device comprising a suture, staple, vascular graft, suture knot clip, orthopedic pin, clamp, screw, plate or clip, and the tissue adhesive or sealant composition of claim 1.

15. A method for sealing tissue, comprising the steps of:
(a) reacting a cross-linking agent of formula 1 comprising:

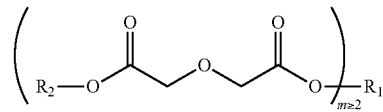

(1) a linker moiety comprising a diglycolic acid;
(2) a water soluble core moiety $R_1$ derived from a compound of the group consisting of tertiary amines or polyethylene glycols, said water soluble core moiety having a plurality of side chain arms with at least two of the side chain arms covalently bonded to the linker moiety (1); and
(3) a group $R_2$ that is covalently bonded to a carboxyl group of the diglycolic acid linker moiety forming an active ester electrophile, and a nucleophilic group-containing protein component, in the presence of moisture to form an adhesive or sealant, and
(b) contacting the adhesive or sealant or its reactants with a tissue surface prior to, during, or after reacting the crosslinking agent with the nucleophilic group-containing protein in the presence of moisture.

* * * * *